United States Patent
Seidl

(10) Patent No.: US 10,854,889 B2
(45) Date of Patent: Dec. 1, 2020

(54) FILM STRUCTURE FOR A BATTERY FOR PROVIDING ON A ROUND BODY

(71) Applicant: Schreiner Group GmbH & Co. KG, Oberschleissheim (DE)

(72) Inventor: Peter Seidl, Munich (DE)

(73) Assignee: Schreiner Group GmbH & Co. KG, Oberschleissenheim (DE)

( * ) Notice: Subject to any disclaimer, the term of this patent is extended or adjusted under 35 U.S.C. 154(b) by 185 days.

(21) Appl. No.: 16/072,567

(22) PCT Filed: Dec. 19, 2016

(86) PCT No.: PCT/EP2016/081771
§ 371 (c)(1),
(2) Date: Jul. 25, 2018

(87) PCT Pub. No.: WO2017/129324
PCT Pub. Date: Aug. 3, 2017

(65) Prior Publication Data
US 2019/0044155 A1    Feb. 7, 2019

(30) Foreign Application Priority Data
Jan. 26, 2016  (DE) .......................... 10 2016 101 325

(51) Int. Cl.
*H01M 6/40* (2006.01)
*H01M 6/10* (2006.01)
(Continued)

(52) U.S. Cl.
CPC ................ *H01M 6/40* (2013.01); *G09F 3/02* (2013.01); *G09F 3/10* (2013.01); *H01M 6/10* (2013.01);
(Continued)

(58) Field of Classification Search
None
See application file for complete search history.

(56) References Cited

U.S. PATENT DOCUMENTS 5,055,968 A   10/1991 Nishi et al.
5,582,931 A   12/1996 Kawakami
(Continued)

FOREIGN PATENT DOCUMENTS

DE          10313006 A1   10/2004
DE    10 2005 017682 A1   10/2006
(Continued)

OTHER PUBLICATIONS

International Search Report of PCT/EP2016/081771, dated Feb. 9, 2017.
(Continued)

*Primary Examiner* — Tracy M Dove
(74) *Attorney, Agent, or Firm* — Collard & Roe, P.C.

(57) ABSTRACT

A film structure for a battery for providing on a round body includes a carrier film, having a first section and a second section following the first section and a third section following the second section. The film structure has a first layer sequence of several layers, having a first electrode layer for forming an anode or a cathode, and a second layer sequence of several layers, having a second electrode layer for forming an anode or cathode different from the first electrode layer. The first and the second layer sequences are arranged on different sections of the carrier film in such a way that the first and the second layer sequences come in contact with each other and the film battery is thereby activated only once a body is labeled.

14 Claims, 2 Drawing Sheets

Figure 1:
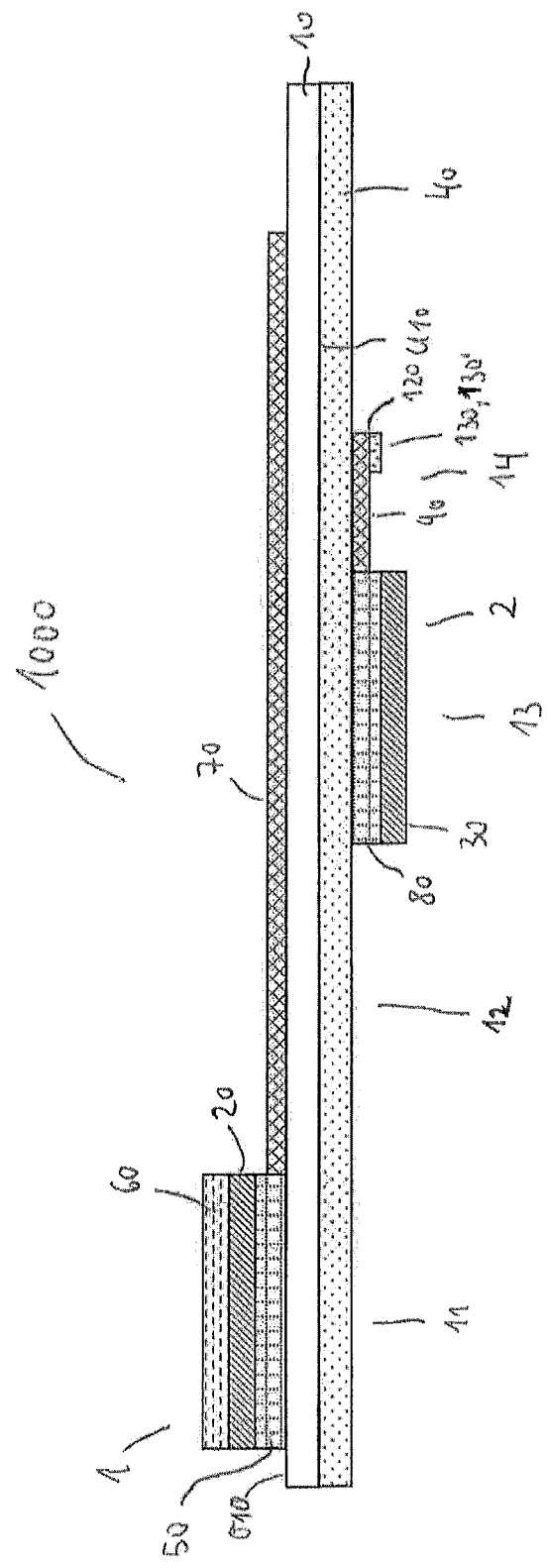

(51) Int. Cl.
  *H01M 10/04* (2006.01)
  *G09F 3/02* (2006.01)
  *G09F 3/10* (2006.01)
  *A61M 5/20* (2006.01)

(52) U.S. Cl.
  CPC .......... *H01M 10/0431* (2013.01); *A61M 5/20* (2013.01); *G09F 2003/0272* (2013.01)

(56) References Cited

U.S. PATENT DOCUMENTS

| | | |
|---|---|---|
| 6,045,942 A | 4/2000 | Miekka et al. |
| 6,136,468 A | 10/2000 | Mitchell, Jr. et al. |
| 6,379,835 B1 | 4/2002 | Kucherovsky et al. |
| 6,752,842 B2 | 6/2004 | Luski et al. |
| 6,780,208 B2 | 8/2004 | Hopkins et al. |
| 7,022,431 B2 | 4/2006 | Shchori et al. |
| 7,320,845 B2 | 1/2008 | Zucker |
| 7,776,471 B2 | 8/2010 | Kim et al. |
| 8,029,927 B2 | 10/2011 | Tucholski |
| 8,268,475 B2 | 9/2012 | Tucholski |
| 8,557,426 B2 | 10/2013 | Lee et al. |
| 2003/0036003 A1 | 2/2003 | Shchori et al. |
| 2003/0099882 A1 | 5/2003 | Hampden-Smith et al. |
| 2003/0228517 A1 | 12/2003 | Holl et al. |
| 2005/0260492 A1 | 11/2005 | Tucholski et al. |
| 2010/0081049 A1 | 4/2010 | Holl et al. |
| 2010/0178551 A1 | 7/2010 | Kreutzer |
| 2011/0086260 A1 | 4/2011 | Kohlberger et al. |
| 2011/0111292 A1 | 5/2011 | Kwon et al. |
| 2012/0058378 A1 | 3/2012 | Lee et al. |
| 2014/0308574 A1 | 10/2014 | Ensling et al. |
| 2015/0136631 A1 | 5/2015 | Seidl |

FOREIGN PATENT DOCUMENTS

| | | |
|---|---|---|
| DE | 10 2008 011523 A1 | 8/2009 |
| DE | 10 2008 023571 A1 | 11/2009 |
| DE | 10 2010 018071 A1 | 10/2011 |
| DE | 10 2010 023092 A1 | 12/2011 |
| DE | 10 2012 102804 B3 | 2/2013 |
| DE | 10 2011 086899 A1 | 5/2013 |
| DE | 10 2012 104460 A1 | 11/2013 |
| EP | 0 602 976 A1 | 6/1994 |
| EP | 0 902 737 B1 | 1/2008 |
| EP | 1 359 633 B1 | 9/2009 |
| EP | 1 485 960 B1 | 6/2011 |
| EP | 2 067 193 B1 | 5/2013 |
| JP | 2007-286717 A | 11/2007 |

OTHER PUBLICATIONS

International Search Report of PCT/EP2016/081767, dated Feb. 24, 2017.

FILM STRUCTURE FOR A BATTERY FOR PROVIDING ON A ROUND BODY

CROSS REFERENCE TO RELATED APPLICATIONS

This application is the National Stage of PCT/EP2016/081771 filed on Dec. 19, 2016, which claims priority under 35 U.S.C. § 119 of German Application No. 10 2016 101 325.0 filed on Jan. 26, 2016, the disclosure of which is incorporated by reference. The international application under PCT article 21(2) was not published in English.

The invention relates to a film structure for a battery to be dispensed onto a round body.

With the development of printed batteries, applications in which electrical functions are supposed to be accommodated on round bodies, such as auto-injectors, for example, in other words syringes having a "movable" needle, which is situated within a housing before the injection and can be moved out of the housing into the skin during the injection, by means of a suitable mechanism, vials, in other words small medication bottles, which are closed off with a rubber stopper, for example, from which a dose is withdrawn by means of a syringe and subsequently injected into the patient, bottles or similar substrates, are moving into the center point to an increasing degree. These functions include, for example, heating systems or display of the expiration of a preparation that is accommodated in the round body, as well as indicators for use of the preparation in the round body or fill levels of a liquid that has been filled into the round body. In the case of applications in which these functions must be supported by a power source, the use of a printed battery on the surface of the round body is practical.

Currently, printed batteries have multiple layers, which are disposed one on top of the other. During application onto the surface of a round body, the layers shift when the battery is bent around the round body. Since in most cases printed batteries are what are called "closed" systems, which generally have at least one "moist" component, printed batteries can only be used on the surfaces of round bodies if they are glued very narrowly along the longitudinal direction. However, since the area size has a significant influence on the performance capacity of the battery, this is only possible for a few applications. In the case of very tight radii, printed batteries are completely eliminated for round bodies.

It is a concern of the present invention to indicate a film structure for a battery to be dispensed onto a round body, wherein the film structure can be easily and reliably applied to the round body, while guaranteeing the functionality of the battery.

An embodiment of a film structure for a battery that is suitable for being dispensed onto a round body is indicated in claim 1.

The film structure for a battery to be dispensed onto a round body comprises a carrier film having a first section and a second section that follows the first section, as well as a third section that follows the second section. The film structure furthermore comprises a first layer sequence composed of multiple layers, having a first electrode layer for forming an anode or a cathode. Furthermore, the film structure has a second layer sequence composed of multiple layers, having a second electrode layer for forming an anode if the first electrode layer is formed as a cathode or a cathode if the first electrode layer is formed as an anode. The first layer sequence is disposed on a top side of the first section of the carrier film. The second layer sequence is disposed on an underside of the third section of the carrier film.

In the dispensing direction, the film structure has the second section of the carrier film following the first section of the carrier film. In the dispensing direction, the third section of the carrier film is disposed following the second section of the carrier film. The first and the third section of the carrier film are therefore disposed so that they are spaced apart from one another by the length of the second section of the carrier film. The first layer sequence is disposed on the carrier film at a first position, and the second layer sequence is disposed on the carrier film at a second position. In this regard, the first and the second position are disposed on the carrier film spaced apart from one another in such a manner that the second electrode layer is disposed above the first electrode layer when the film structure is wound around the round body, if, in the dispensing direction, first the first section of the carrier film and subsequently the second section and finally the third section of the carrier film are wound around the round body.

The film structure comprises an electrolyte layer that is disposed between the first and second electrode layer when the second layer sequence is disposed on top of the first layer sequence when the film structure is wound around the round body. When the second electrode layer is disposed on the first electrode layer spaced apart from it by the thickness of the electrolyte layer, activation of the battery takes place, to make a voltage available.

In the case of the film structure, the battery is only activated to generate a voltage or for ion transport between the electrode layers when the film structure is wound around the round body and the second layer sequence is disposed on top of the first layer sequence. Only after label placement onto the round body, the first and second electrode layer therefore lie one on top of the other in such a manner that the first electrode layer can form an anode, for example, and the second electrode layer can form a cathode of the activated battery.

The first and the second electrode layer act as current-forming surfaces. To tap a voltage that is made available by the battery in the activated state, conductive tracks can be disposed underneath the respective current-forming surfaces of the first and second layer sequence. These conductor tracks can be imprinted onto the underside of the carrier film, for example, for a connection with the first electrode layer on the top side and for a connection with the second electrode layer.

Since the conductive tracks must be applied underneath the respective current-forming surfaces, a production method can be used in which the carrier film is imprinted from above and covered, and then the material web is turned. The electrolyte layer required for activation of the battery is applied to the current-forming surface/first electrode layer on the top side of the first section of the carrier film, for example, or onto the current-forming surface/second electrode layer on the underside of the third section of the carrier film. This can take place, for example, by imprinting the electrolyte layer onto one of the electrode layers. If necessary, the electrolyte layer is temporarily sealed, for example with a protective film. The seal is removed again before placement of the label.

To tap a voltage that is made available by way of the conductor tracks that are disposed on the top side and underside of the carrier film, conductive connection surfaces can be provided on the top side and on the underside of the carrier film. After label placement, the connection surfaces at first lie opposite one another on different sides of the carrier film.

Since in most cases it is necessary that both connection surfaces are situated on one side of the carrier film and not on different sides of the carrier film, in order for contacting or tapping of the voltage to take place at the connection surfaces, a further conductor track can be placed on one side of the carrier film, for example on the top side of the carrier film, in addition to the conductor track disposed there, according to a preferred embodiment. Both conductor tracks are disposed on the same side of the carrier film, at a distance from one another.

An electrically conductive connection surface for tapping a voltage can be disposed at one end of the further conductor track. An electrically conductive contact surface is disposed at the other end of the further conductor track. A further electrically conductive contact surface is disposed at the end of the conductor track disposed on the other side of the carrier film, which track is connected with the electrode layer disposed on this side of the carrier film. The two contact surfaces are disposed on the opposite sides of the carrier film in such a manner that the two contact surfaces are disposed one on top of the other on the round body to be labeled, and stand in electrical contact with one another after application of the film structure.

In order for the two contact surfaces to adhere to one another, an electrically conductive adhesive, for example an anisotropically conductive adhesive paste, can be applied to at least one of the contact surfaces. A corresponding pressure and the required high temperature, for example a temperature of 120° C., can be briefly made available by means of a hot-embossing device on a labeling machine, in order to make the connection between the two contact surfaces conductive. Thereby a voltage potential of the voltage to be tapped after labeling of the round body can be transferred from one side of the carrier film to the other side of the carrier film, so that voltage tapping by way of the connection surfaces is only possible on one side of the carrier film.

As an alternative to an electrically conductive adhesive between the contact surfaces, a contact adhesive that is configured to be dry can be used. An offset adhesive grid can be applied, in particular imprinted, onto this adhesive. A continuous self-sticking adhesive with great adhesive force is imprinted onto the underside of the carrier film. In between, there is a region in which the second contact surface is imprinted, onto which in turn the second grid composed of the conductive paste is then imprinted. Now the adhesive force of the two dry contact adhesive layers is sufficient to hold the two contact surfaces together in conductive manner. Additional pressure is produced by the label application, thereby supporting contacting.

The invention will be illustrated and explained in greater detail below, using figures, which show exemplary embodiments of the present invention. The figures show:

FIG. 1 a cross-section through an embodiment of a film structure for a battery to be dispensed onto a round body.

Figure 2:
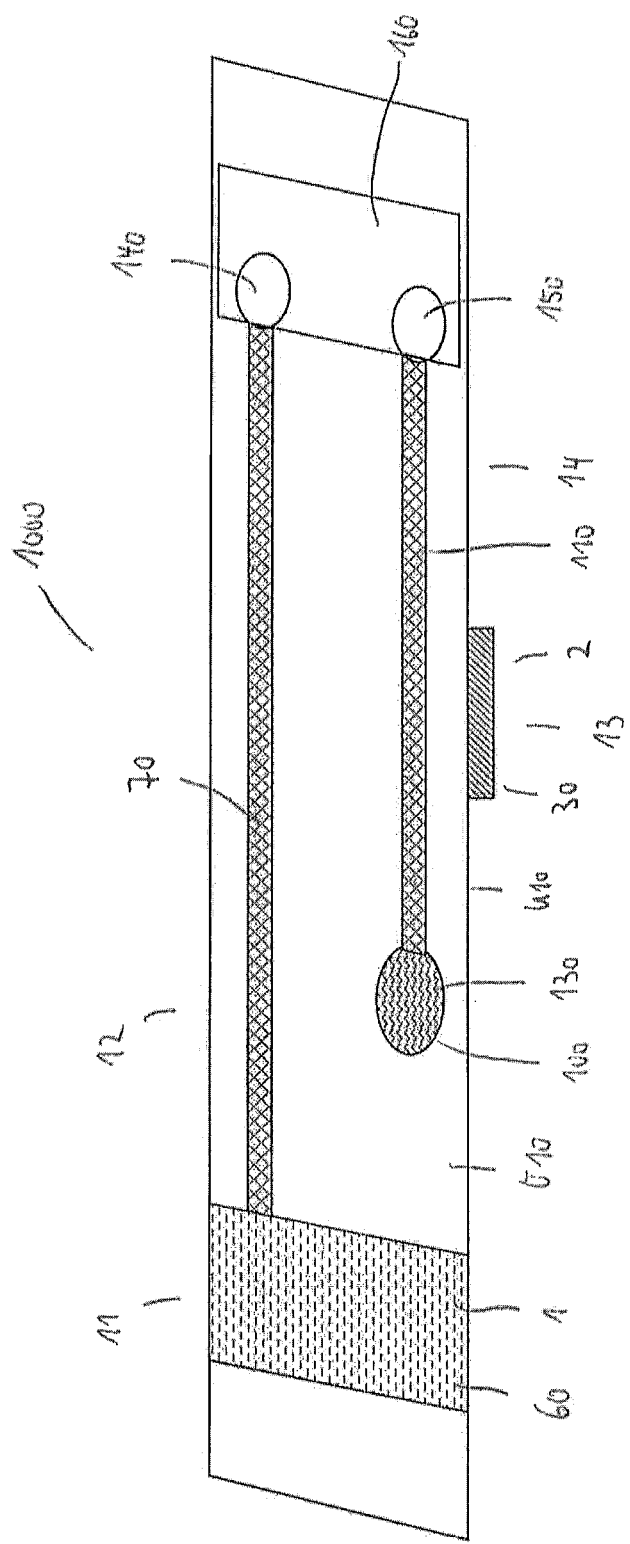

FIG. 2 a perspective view of an embodiment of the film structure for a battery to be dispensed onto a round body.

FIG. 1 shows an embodiment of a film structure 1000 for a printed battery to be dispensed onto a round body. FIG. 2 shows a top view of the film structure 1000. The structure as well as the function of the film structure for the printed battery will be described below, using FIGS. 1 and 2.

The film structure 1000 has a carrier film 10 having a first section 11 and a second section 12 that follows the first section, as well as a third section 13 that follows the second section. The film structure has a first layer sequence 1 that comprises multiple layers. One of the layers of the first layer sequence 1 is an electrode layer 20 for forming an anode or a cathode of the battery implemented with the film structure. Furthermore, the film structure 1000 comprises a second layer sequence 2 composed of multiple layers, having an electrode layer 30 for forming an anode if the first electrode layer 20 is formed as a cathode, in other words acts as a cathode after label application of the film structure, or acts as a cathode if the electrode layer 20 is formed as an anode, in other words has the function of an anode after label application of the film structure.

The first layer sequence 1 is disposed on a top side O10 of the first section 11 of the carrier film 10. The second layer sequence 2 is disposed on an underside U10 of the third section 13 of the carrier film 10. The electrode layer 20 can have zinc or manganese or manganese dioxide as a conductive material, for example. Likewise, the electrode layer 30 can have zinc, manganese or manganese dioxide. The electrode layer 20 can be formed from a different material than the electrode layer 30. For example, the electrode layer 20 can contain zinc, and the electrode layer 30 can contain manganese.

The film structure has an adhesive layer 40 on the underside U10 of the carrier film 10. The region of the adhesive layer 40 that is disposed on the underside U10 of the first section 11 of the carrier film 10 serves to glue the film structure onto the round body, during label application of the film structure, if the length of the first section 11 of the carrier film corresponds to the length of a circumference line of the round body.

The first layer sequence 1 comprises an electrolyte layer 60 which can be disposed above the electrode layer 20, as shown in FIG. 1. However, it is also possible to provide the electrolyte layer 60 in the second layer sequence 2 and to dispose it under the electrode layer 30, according to the representation in FIG. 1. In this embodiment, the electrolyte layer 60 is the outermost layer of the layer sequence 2.

The electrolyte 60 is a medium that makes an ion stream possible between the electrode layers 20 and 30 in the activated state of the battery, in other words when the second layer sequence 2 is disposed on top of the first layer sequence 1 after having been wrapped around the round body to be labeled. The electrolyte of the layer 60 can be configured as a paste-like electrolyte, for example, which is temporarily sealed in by means of a releasably adhesive film, for example a siliconized protective film.

Alternatively, the electrolyte of the layer 60 can be configured as a "dry" electrolyte. In the latter case, providing a covering over the electrolyte layer 60 is not necessary. The "dry" electrolyte is moistened immediately before label application.

According to one embodiment, a separator, for example in the form of a lattice structure and/or a point structure and/or a honeycomb structure and/or a cross-hatching can be provided between the electrode layers 20 and 30, to prevent the two electrode layers 20 and 30 from touching in the activated state of the battery, when the electrode layers 20 and 30 are disposed one on top of the other, after the film structure has been wound around the round body. An insulation varnish, for example, can be used for the separator. For example, the electrolyte 60 fills the spaces that are not already covered by the separator. For reasons of a simplified representation, the separator is not shown in the film structure shown in FIG. 1. It should be noted, however, that the battery also functions without a separator if the electrolyte layer is disposed between the electrode layers.

The first layer sequence 1 has a first conductive contact layer 50, which is disposed on the top side O10 of the first section 11 of the carrier film 10, between the carrier film 10 and the electrode layer 20. Likewise, the second layer sequence 2 has a conductive contact layer 80, which is disposed on the underside U10 of the third section 13 of the carrier film, between the carrier film 10 and the electrode layer 30. The first and the second conductive contact layer can each contain carbon.

The first and the second layer sequence are disposed on the top side and underside of the carrier film, at different positions. The positions are selected as a function of the circumference of the round body to be labeled, in such a manner that the two layer sequences 1 and 2 lie one on top of the other after label application, and thereby the battery is activated.

According to a possible embodiment, the first layer sequence 1 can be disposed at a first position on the first section 11 of the carrier film. The second layer sequence 2 can be disposed at a second position on the third section 13 of the carrier film. The first and the second position are disposed at a distance from one another, in such a manner that the electrode layer 30 is disposed above the electrode layer 20 when the film structure 1000 is wound around a round body to be labeled, if, in the dispensing direction, first the first section 11 of the carrier film 10 is wound around the round body, subsequently the second section 12 and after that the third section 13 of the carrier film are wound around the round body.

According to a possible embodiment of the film structure, the first layer sequence 1 can be disposed on the first section 11 of the carrier film 10 at the first position, and the second layer sequence 2 can be disposed on the third section 13 of the carrier film 10 at the second position, at a distance from one another, in such a manner that the electrode layer 30 lies on the electrolyte layer 60 when the film structure 1000 is wound around the round body to be labeled, if, in the dispensing direction, first the first section 11 of the carrier film and subsequently the second section 12 and after that the third section 13 of the carrier film are wound around the round body.

The film structure 1000 has a first conductor track 70 for conducting a current to/from the first electrode layer 20. The first conductor track 70 is disposed on the top side O10 of the carrier film 10 and connected with the first contact layer 50. Furthermore, the film structure 1000 has a second conductor track 90 for conducting a current to/from the electrode layer 30. In FIG. 1, the conductor track 70 is disposed on the top side O10 of the carrier film, above the conductor track 90. This representation was selected to show both conductor tracks in cross-section through the film structure in one figure. However, the conductor tracks 70 and 90 are disposed on the top side and the underside of the carrier film, not one on top of the other, but rather laterally offset relative to one another.

The carrier film 10 has a fourth section 14 that follows the third section 13 in the dispensing direction. The second conductor track 90 is disposed on the underside U10 of the fourth section 14 of the carrier film 10 and connected with the second conductive contact layer 80.

The film structure 1000 has a first electrically conductive contact surface 100 that is disposed on the top side O10 of the second section 12 of the carrier film 10. Furthermore, the film structure 1000 has a third conductor track 110, which is disposed on the top side O10 of the carrier film 10 and is connected with the first contact surface 100. The first contact surface 100 can be formed, for example, in that the third conductor track 110 has a widened section at its end. The first conductor track 70 and the third conductor track 110 are disposed at a distance from one another on the top side O10 of the second section 12 and of the third section 13 of the carrier film 10. Furthermore, the first and the third conductor track 70, 110 can additionally also be continued on the top side O10 of the fourth section 14 of the carrier film 10, and also be disposed at a distance from one another there.

According to a possible embodiment, the film structure 1000 can have a second electrically conductive contact surface 120, which is disposed on the underside U10 of the fourth section 14 of the carrier film 10. The second conductor track 90 can be connected with the second contact surface 120 with a first end, and with the second conductive contact surface 80 with a second end. The second contact surface 120 can be formed, for example, in that the second conductor track 90 has a widened section at the first end. The second contact surface 120 is disposed on the underside U10 of the fourth section 14 of the carrier film 10, in such a manner that the first contact surface 100 lies on the second contact surface 120 when the fourth section 14 of the carrier film 10 lies on the second section 12 of the carrier film during dispensing of the film structure 1000 onto the round body to be labeled.

As a result, a current can be transferred from the electrode layer 30, by way of the conductor track 90, to the second contact surface 120, and from there, by means of the conductive connection with the first contact surface 100, to the top side O10 of the carrier film, if the battery is activated, i.e. if the fourth section 14 of the carrier film 10 lies on the second section 12 of the carrier film 10 during dispensing of the film structure 1000 onto the round body.

According to a possible embodiment, the first and the second contact surface 100, 120 can have a conductive material. The conductive material of at least one of the first and the second contact surface 100, 120 can be coated with a conductive adhesive 130'. When the second section and the fourth section of the carrier film are pressed against one another, the first and the second contact surface thereby adhere to one another and represent an electrically conductive connection. As a result, it is possible to transfer the current flow of a pole of the battery to the other side of the carrier film, so that connection surfaces 140, 150, which are situated at the end of the first conductor track and the third conductor track, for example, lie in one plane.

According to an alternative embodiment, the first and the second contact surface 100, 120 can each have a dry adhesive 130 and a conductive material. A dry adhesive is an adhesive that adheres only to itself. The respective conductive material of the first and the second contact surface 100, 120 can be disposed on the respective dry adhesive 130 of the first and second contact surface 100, 120. If now the fourth section 14 of the carrier film 10 is disposed on the second section 12 of the carrier film during dispensing of the film structure 1000 onto the round body to be labeled, the dry adhesive 130 of the first contact surface 100 adheres to the dry adhesive 130 of the second contact surface 120, and the conductive material of the first contact surface 100 is thereby electrically contacted with the conductive material of the second contact surface 120.

As a result, it is possible in this embodiment, as well, to transfer the current flow of the electrode layer 30 that acts as a cathode, for example, from the underside U10 of the carrier film to the top side O10 of the carrier film, in order to thereby tap a voltage made available by the activated battery at respective connection surfaces 140, 150, which are connected with the first conductor track 70 and the third conductor track 110, respectively.

As has already been mentioned above, electrically conductive connection surfaces 140, 150 can be disposed on the top side O10 of the carrier film 10, which surfaces are connected with a respective end of the conductor tracks 170 and 110. The connection surfaces can be formed, for example, in that the conductor tracks 70 and 110 are widened at their end. It is possible, according to a further embodiment, to connect the film battery directly with an electrical component 160, for example an electronic display device, in order to supply the electrical component with an operating voltage.

With the film structure 1000 as indicated, it is possible to implement a printed battery that can be rolled up, overlapping, and adhesively connected. The film structure is adapted to the body to be labeled, preferably a round body, so that when the film structure is wound around the body to be labeled, the first section 11 and the second section 12 of the carrier film adhere to the surface of the body to be labeled, and the third section 13 lies on the first section 11, and the fourth section 14 lies on the second section 12 of the carrier film.

With the film structure, a film battery with high performance values can be implemented, which battery can be applied to radii of any circumference of a body to be labeled, without tensions. A battery produced in this manner can be combined with other printed electronic components, for example a heating component, a light component, or a display, or can also be equipped with electronic components. The result is a film strip adhesively applied around a labeled round body, having one or more of the functions described above.

REFERENCE SYMBOL LIST 10 carrier film
20 electrode layer
30 electrode layer
40 adhesive layer
50 first conductive contact layer
60 electrolyte layer
70 first conductor track
80 second conductive contact layer
90 second conductor track
100 first contact surface
110 third conductor track
120 second contact surface
130 connection surface
140 connection surface
150 connection surface

The invention claimed is:

1. A film structure for a battery to be dispensed onto a round body, comprising:
a carrier film having a first section and a second section that follows the first section, and a third section that follows the second section,
a first layer sequence composed of multiple layers, having a first electrode layer for forming an anode or a cathode,
a second layer sequence composed of multiple layers, having a second electrode layer for forming the anode if the first electrode layer is formed as the cathode or the cathode if the first electrode layer is formed as the anode, and
an adhesive layer that is disposed on an underside of the carrier film,
wherein the first layer sequence is disposed on a top side of the first section of the carrier film,
wherein the second layer sequence is disposed on the underside of the third section of the carrier film.

2. The film structure according to claim 1, wherein the first layer sequence is disposed on the first section of the carrier film at a first position, and the second layer sequence is disposed on the third section of the carrier film at a second position, spaced apart from one another in such a manner that the second electrode layer is disposed above the first electrode layer when the film structure is wound around the round body, if, in a dispensing direction, first the first section of the carrier film is wound around the round body, and subsequently the second section and the third section of the carrier film are wound around the round body.

3. The film structure according to claim 1, wherein the first layer sequence has a first conductive contact layer, which is disposed on the top side of the first section of the carrier film, between the carrier film and the first electrode layer.

4. The film structure according to claim 1, wherein the first layer sequence comprises an electrolyte layer, which is disposed above the first electrode layer.

5. The film structure according to claim 4, wherein the first layer sequence is disposed on the first section of the carrier film at a first position, and the second layer sequence is disposed on the third section of the carrier film at a second position, spaced apart from one another in such a manner that the second electrode layer lies on the electrolyte layer when the film structure is wound around the round body, if, in a dispensing direction, first the first section of the carrier film and subsequently the second section and the third section of the carrier film are wound around the round body.

6. The film structure according to claim 1, comprising:
a first conductor track for conducting a current to/from the first electrode layer,
wherein the first conductor track is disposed on the top side of the carrier film and connected with a first contact layer.

7. The film structure according to claim 1, wherein the second layer sequence comprises a second conductive contact layer, which is disposed on the underside of the third section of the carrier film, between the carrier film and the second electrode layer.

8. The film structure according to claim 1, comprising:
a second conductor track for conducting a current to/from the second electrode layer,
wherein the carrier film has a fourth section that follows the third section,
wherein the second conductor track is disposed on the underside of the fourth section of the carrier film and connected with a second conductive contact layer.

9. The film structure according to claim 1, comprising:
a first contact surface, which is disposed on the top side of the second section of the carrier film,
a third conductor track, which is disposed on the top side of the carrier film and connected with the first contact surface.

10. The film structure according to claim 9, wherein a first and the third conductor track are disposed on the top side of the second and the third section of the carrier film, at a distance from one another.

11. The film structure according to claim 8, comprising:
a second contact surface which is disposed on the underside of the fourth section of the carrier film, wherein the second conductor track is connected with the second contact surface with a first end, and with a second conductive contact layer with a second end.

12. The film structure according to claim 11, wherein the second contact surface is disposed on the underside of the fourth section of the carrier film, in such a manner that a first contact surface lies on the second contact surface, and thereby a current is transferred from the second electrode layer to the second contact surface when the fourth section of the carrier film lies on the second section of the carrier film when the film structure is dispensed onto the round body.

13. The film structure according to claim 11,
wherein a first and second contact surface each have a dry adhesive and a conductive material, wherein the respective conductive material of the first and second contact surface is disposed on the respective dry adhesive of the first and second contact surface,
wherein the dry adhesive of the first contact surface adheres to the dry adhesive of the second contact surface, and the conductive material of the first contact surface is electrically contacted with the conductive material of the second contact surface if the fourth section of the carrier film is disposed on the second section of the carrier film during dispensing of the film structure onto the round body.

14. The film structure according to claim 11,
wherein a first and the second contact surface have a conductive material,
wherein the conductive material of at least one of the first contact surface or the second contact surface is coated with a conductive adhesive.

\* \* \* \* \*

UNITED STATES PATENT AND TRADEMARK OFFICE
CERTIFICATE OF CORRECTION

PATENT NO. : 10,854,889 B2  
APPLICATION NO. : 16/072567  
DATED : December 1, 2020  
INVENTOR(S) : Seidl Page 1 of 1

It is certified that error appears in the above-identified patent and that said Letters Patent is hereby corrected as shown below:

On the Title Page

Column 1, item (73), the spelling of the city of the Assignee should correctly read as follows:
-- Oberschleissheim --.

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*